United States Patent [19]

Perren

[11] Patent Number: 4,874,243
[45] Date of Patent: Oct. 17, 1989

[54] APPARATUS FOR CONTINUOUSLY MEASURING THE TURBIDITY OF A FLUID

[76] Inventor: Benno Perren, Austrasse 33, 5430 Wettingen, Switzerland

[21] Appl. No.: 194,990

[22] PCT Filed: Aug. 26, 1987

[86] PCT No.: PCT/CH87/00108
§ 371 Date: Apr. 25, 1988
§ 102(e) Date: Apr. 25, 1988

[87] PCT Pub. No.: WO88/01737
PCT Pub. Date: Mar. 10, 1988

[30] Foreign Application Priority Data
Sep. 1, 1986 [CH] Switzerland .............. 3505/86

[51] Int. Cl.$^4$ .............. G01N 21/15; G01N 21/53
[52] U.S. Cl. .............. 356/342; 250/574; 356/440
[58] Field of Search .......... 356/440, 441, 442, 342; 250/574, 576

[56] References Cited

U.S. PATENT DOCUMENTS

| | | | |
|---|---|---|---|
| 3,496,366 | 2/1970 | Hunziker et al. | 356/242 X |
| 3,714,444 | 1/1973 | Carr et al. | 356/442 |
| 3,861,198 | 1/1975 | Shea | 356/246 X |
| 4,343,552 | 8/1982 | Blades | 350/584 |

FOREIGN PATENT DOCUMENTS

| | | | |
|---|---|---|---|
| 2433355 | 1/1976 | Fed. Rep. of Germany | 356/442 |
| 2567645 | 1/1986 | France . | |

*Primary Examiner*—Vincent P. McGraw
*Attorney, Agent, or Firm*—Werner W. Kleeman

[57] ABSTRACT

In the measuring chamber the flow of the fluid to be monitored impinges at an angle upon the end window of the measuring probe. Due to the thus occurring self-cleaning action, no deposit forms at the end window and which deposit would falsify the meaurement. In the event of small fluid quantity throughputs and flow rate and thus insufficient cleaning action, a nozzle is provided for producing a jet which is directly aimed at the end window. The fluid is irradiated in the region of the measuring probe by using ray guides. If particles causing turbidity are contained in the fluid, the rays will be reflected, collected by the optical system and supplied to a receiver through a ray guide.

14 Claims, 1 Drawing Sheet

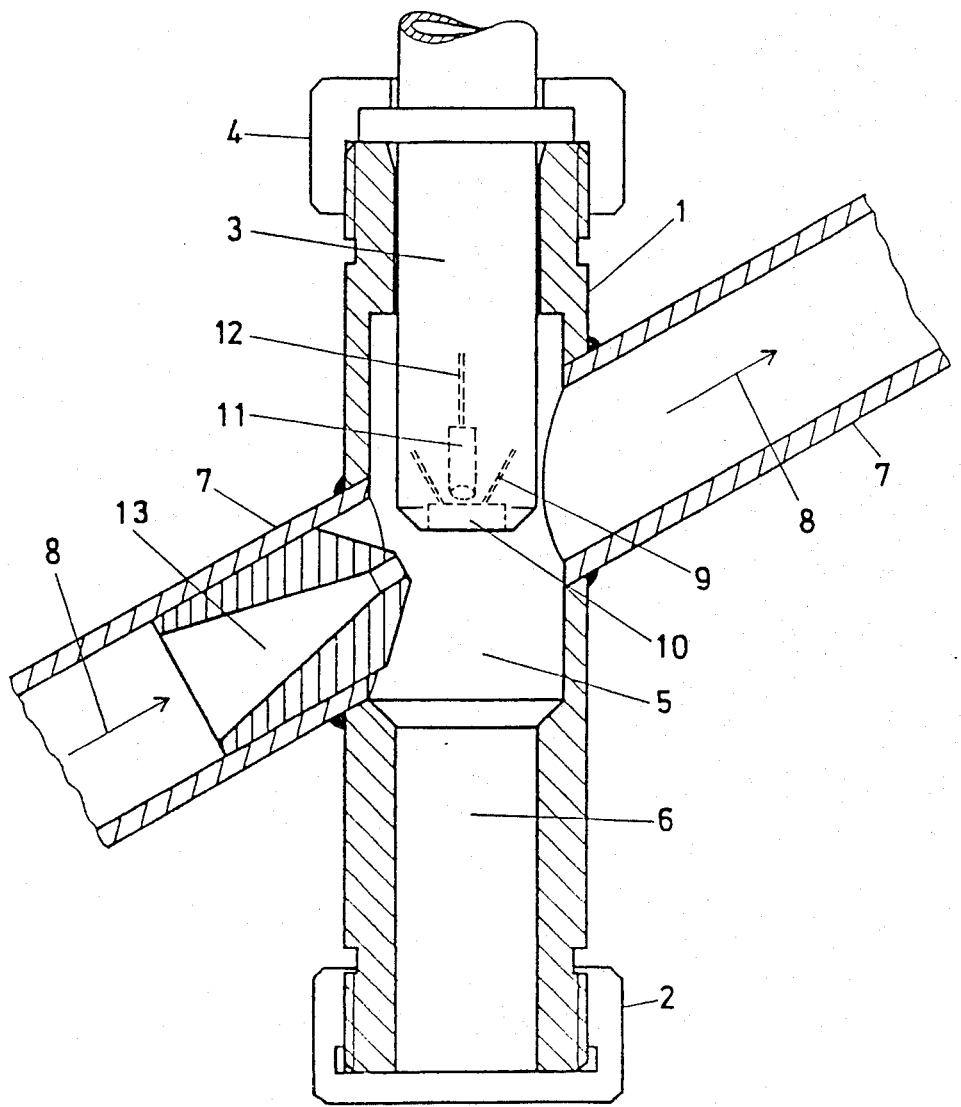

APPARATUS FOR CONTINUOUSLY MEASURING THE TURBIDITY OF A FLUID

BACKGROUND OF THE INVENTION

The present invention relates to a new and improved method of, and apparatus for, continuously measuring the turbidity of a fluid which contains particles causing such turbidity.

In its more particular aspects the present invention specifically relates to a new and improved method of, and apparatus for, continuously measuring turbidity of a fluid which contains particles causing such turbidity, with the aid of a measuring probe which comprises a window and a built-in optical system for evaluating or appraising the fluid which is irradiated at least in the region of the measuring probe.

For measuring the turbidity of a a contaminated fluid there is generally used a measuring probe for irradiating the fluid which flows by or is present in a container. The rays reflected by the particles causing turbidity are collected by an optical system built into the measuring probe and fed to a receiver where the intensity of the reflected rays is detected and eventually necessary control steps are initiated.

In such apparatus it is disadvantageous that the end window of the measuring probe and which end window comes into contact with the fluid, is quickly covered by the particles contained in the fluid. Thus the maintenance intervals, even in compensated systems, are mainly determined by the contamination of the end window. A further disadvantage lies in the fact that, due to the covered end window, the measurement is falsified in the sense of a seemingly stronger reflection.

SUMMARY OF THE INVENTION

Therefore, with the foregoing in mind it is a primary object of the present invention to provide a new and improved method of, and apparatus for, continuously measuring turbidity of a fluid which contains particles causing such turbidity, and which method and apparatus are not afflicted with the drawbacks and limitations of the prior art heretofore discussed.

Another significant object of the present invention is directed to a new and improved method of, and apparatus for, continuously measuring turbidity of a fluid which contains particles causing such turbidity, and which method and apparatus permit obtaining unobjectionable measuring results over long time periods of use of the measuring apparatus.

Yet a further important object of the present invention aims at providing a new and improved construction of an apparatus for continuously measuring turbidity of a fluid which contains particles causing such turbidity, and which apparatus is simple in construction and design, quite economical to manufacture, highly reliable in operation, not readily subject to breakdown or malfunction and requires a minimum of maintenance and servicing.

Now in order to implement these and still further objects of the invention, which will become more readily apparent as the description proceeds, the apparatus of the present development is manifested, among other things, by the features that, a measuring chamber is throughpassed by at least a partial flow of the fluid to be investigated. The measuring probe is arranged in a manner such that the at least partial flow of the fluid to be investigated impinges upon an end window of the measuring probe at a predetermined impingement angle.

As alluded to above, the invention is not only concerned with the aforementioned apparatus aspects, but also relates to a novel method of continuously measuring turbidity of a fluid which contains particles causing such turbidity.

To achieve the afore-mentioned measures, the inventive method, in its more specific aspects, comprises evaluating, as a measure of the turbidity of the fluid, the intensity of the rays which are reflected by the irradiated fluid and received by the optical system of the measuring probe.

Due to the continuous rinsing of the end window in the inventive construction and which rinsing may be still intensified by means of a nozzle, there results a mechanical self-cleaning of the end window and practically makes impossible the formation of a deposit on the end window. Precise measuring results are thus obtained and an only occasional examination of the apparatus is recommended for safety reasons. The apparatus can be used for monitoring pure water and service water, condensates and emulsions and likewise industrial waters, in fact, practically any fluid which permits the continuous measurement of turbidity. Fields of application of the apparatus are, for example, water supply and water treatment, sewage treatment, process technology, washing plants etc.

BRIEF DESCRIPTION OF THE DRAWING

The invention will be better understood and objects other than those set forth above will become apparent when consideration is given to the following detailed description thereof. Such description makes reference to the annexed single drawing which shows a schematic sectional view of an exemplary embodiment of the inventive apparatus.

DETAILED DESCRIPTION OF THE PREFERRED EMBODIMENTS

Describing now the drawing, it is to be understood that only enough of the construction of the turbidity measuring apparatus has been shown as needed for those skilled in the art to readily understand the underlying principles and concepts of the present development, while simplifying the showing of the drawing. Turning attention now specifically to the single FIGURE of the attached drawing, there has been illustrated therein by way of example and not limitation a tubular measuring chamber 1 which is totally filled by the fluid to be investigated and closed on one side by a plug 2. On the other side, a measuring probe 3 is inserted and sealingly held by means of a screw cap 4. The measuring chamber 1 comprises a measuring space 5 which is joined by an extension 6 the purpose of which will be indicated hereinafter.

To the measuring chamber 1 there are connected two axially aligned tubes 7 which are throughpassed by the fluid to be investigated in the direction of the arrows 8. The axes of the measuring chamber 1 and of the tubes 7 intersect at an angle which is different from 90°. The measuring chamber 1 and the tubes 7 are fabricated, for example, from PVC and interconnected by adhesive bonding but can also be integrally or conjointly cast in the form of a single crosspiece.

Into the measuring probe 3 there are incorporated two or more ray guides 9 which guide radiation for irradiating the fluid present in the measuring space 5 through the end window 10. Furthermore, an optical system 11 containing a ray guide 12 is accommodated in the measuring probe 3.

The end window 10 can be fabricated from conventional glass, however, is better made of quartz glass or sapphire. Such end window 10 is arranged in a manner such that the fluid flow in the tubes 7 directly impinges upon the end window at a predetermined angle, preferably at an angle of 45°. It is thereby insured that the flowing fluid continuously mechanically cleans the end window 10 so that no deposit can be formed thereupon and falsify or even render impossible the measurement.

If large fluid quantities must be monitored in containers or piping systems, a bypass operation is indicated, that is to say that only a partial quantity of the fluid to be investigated is guided through the measuring chamber 1 and this is sufficient for the evaluation or appraisal of the total fluid volume. If, however, the quantity of fluid which flows through the measuring chamber 1, is too small to reliably prevent deposit formation on the end window 10, then, it is advantageous to install a nozzle 13 in the tube 7 such that the jet exiting from the nozzle 13 is directly aimed at the end window 10. Should there exist the possibility that gas bubbles are formed in the fluid to be investigated or that such gas bubbles are entrained by the fluid, then, it is advantageous to pressurize the fluid in the measuring chamber 1 in order to eliminate or at least reduce the gas bubbles.

The mode of operation of the apparatus according to the invention is as follows:

The measuring chamber 1 is throughpassed by the fluid to be monitored. By means of the ray guides 9, the fluid is irradiated in the region of the measuring probe 3 using, for example, light rays. If particles causing turbidity are contained in the fluid, for instance, particles of solid matter of an emulsion, then, such particles reflect the rays. These reflected rays are collected by the optical system 11 and fed into the ray guide 12 which guides the rays to a (not illustrated) receiver. The intensity of the reflected rays is a measure for the turbidity of the fluid.

With increasing turbidity of the fluid the effective measuring depth is reduced. Individual particles can still be detected at a depth of, for example, 10 cm but at higher turbidity only in the proximity of the end window 10. In order to have available in all cases a sufficient measuring depth, it is advantageous to provide the measuring space 5. Even in the measuring space 5 is not throughpassed by the fluid in its entirety, its contents is nevertheless continuously renewed by the occurring turbulences. The extension 6, which should have a certain depth, is provided in order that possibly occurring reflections of the rays at the walls or at the bottom are avoided as far as possible and sources of error are thus eliminated.

While there are shown and described present preferred embodiments of the invention, it is to be distinctly understood that the invention is not limited thereto, but may be otherwise variously embodied and practiced within the scope of the following claims.

What I claim is:

1. An apparatus for continuously measuring turbidity of a fluid which contains particles causing turbidity, comprising:
   a turbidity measuring device containing a measuring chamber and a measuring probe extending into said measuring chamber;
   throughflow means for throughpassing at least a portion of the fluid to be investigated;
   said throughflow means being connected to said turbidity measuring device for throughpassing said fluid to be investigated through said measuring chamber in a predetermined throughflow direction;
   said measuring probe extending into said measuring chamber, containing an end face located in said measuring chamber and a single end window located at said end face and extending at a predetermined angle relative to said throughflow direction of said fluid to be investigated;
   said throughflow means directing said fluid to be investigated to impinge at a predetermined angle upon said single end window located at said end face of said measuring probe, and at a fluid flow rate sufficient to prevent deposit formation on said single end window;
   radiation guide means contained in said measuring probe for guiding and passing radiation through said single end window located at said end face of said measuring probe for irradiating said fluid to be investigated and throughpassing through said measuring chamber; and
   an optical system contained in said measuring probe and cooperating with said single end window for receiving reflected radiation reflected by turbidity causing particles present in said fluid to be investigated and throughpassing through said measuring chamber.

2. The apparatus as defined claim 1, wherein:
   said throughflow means directing said fluid to be investigated to impinge upon said single end window located at said end face of said measuring probe at an angle of substantially 45°.

3. The apparatus as defined in claim 1, further including:
   a nozzle arranged in said throughflow means for directing said fluid to be investigated to impinge at said predetermined angle upon said single end window located at said end face of said measuring probe; and
   said nozzle being structured to generate said fluid flow rate sufficient for preventing said deposit formation on said single end window located at said end face of said measuring probe.

4. The apparatus as defined in claim 3, wherein:
   said nozzle is arranged in said throughflow means for directing a fluid jet of said fluid to be investigated to impinge at an angle of substantially 45° upon said single end window located at said end face of said measuring probe.

5. The apparatus as defined in claim 1, wherein:
   said measuring chamber defines a measuring space communicating with said throughflow means and facing said single end window located at said end face of said measuring probe.

6. The apparatus as defined in claim 5, further including:
   an extension of said measuring device; and
   said extension extending from said measuring space in a direction substantially opposite to said measuring probe.

7. The apparatus as defined in claim 1, wherein:
   said throughflow means connected to said measuring device for throughpassing said fluid to be investigagted through said measuring chamber, throughpass pressurized fluid through said measuring chamber in order to thereby at least reduce the effect of gas bubbles present in the fluid to be investigated.

8. The apparatus as defined in claim 1, wherein:
said single end window located at said end face of said measuring probe, is made of quartz glass.

9. The apparatus as defined in claim 1, wherein:
said single end window located at said end face of said measuring probe, is made of sapphire.

10. A method of continuously measuring turbidity of a fluid which contains particles causing turbidity, comprising the steps of:
throughpassing at least a portion of the fluid to be investigated in a predetermined throughflow direction through a measuring chamber of a turbidity measuring device;
during said step of throughpassing said fluid to be investigated through said measuring chamber, irradiating said throughpassing fluid through a single end window located at an end face of a measuring probe of the turbidity measuring device;
during said step of throughpassing said fluid to be investigated through said measuring chamber, directing said fluid to be investigated to impinge at a predetermined angle upon said single end window located at said end face of said measuring probe and thereby continuously cleaning said single end window by said impinging fluid to be investigated;
passing radiation through said single end window located at said end face of said measuring probe into said fluid to be investigated and throughpassing through said measuring chamber, and receiving, through said single end window, reflected radiation reflected by turbidity causing particles present in said fluid to be investigated and throughpassing through said measuring chamber; and
measuring said reflected radiation and evaluating said measured reflected radiation for determining the turbidity of said fluid to be investigated and throughpassing through said measuring chamber.

11. The method as defined in claim 10, wherein:
said step of directing said fluid to be investigated to impinge at said predetermined angle upon said single end window located at said end face of said measuring chamber, entails directing said fluid to be investigated to impinge at an angle of substantially 45° upon said single end window located at said end face of said measuring probe.

12. The method as defined in claim 10, wherein:
said step of throughpassing said fluid to be investigated through said measuring chamber entails generating a fluid jet and directing said fluid jet to impinge at said predetermined angle upon said single end window located at said end face of said measuring probe.

13. The method as defined in claim 12, wherein:
said step of generating said fluid jet includes directing said fluid jet to impinge at an angle of substantially 45° upon said single end window located at said end face of said measuring probe.

14. The method as defined in claim 10, wherein:
said step of throughpassing said fluid to be investigated through said measuring chamber includes pressurizing said fluid to be investigated in order to thereby at least reduce the effect of gas bubbles present in said fluid to be investigated.

* * * * *